US00RE45404E

(19) United States
(12) Reissued Patent
Tsutsui

(10) Patent Number: US RE45,404 E
(45) Date of Reissued Patent: Mar. 3, 2015

(54) POWDER MEDICINE APPLICATOR FOR NASAL CAVITY

(75) Inventor: Tatsuo Tsutsui, Kanagawa (JP)

(73) Assignee: Shin Nippon biomedical Laboratories, Ltd., Kagoshima (JP)

(21) Appl. No.: 12/576,219

(22) Filed: Oct. 8, 2009

Related U.S. Patent Documents

Reissue of:
(64) Patent No.: 7,278,982
Issued: Oct. 9, 2007
Appl. No.: 10/550,490
PCT Filed: Mar. 27, 2003
PCT No.: PCT/JP03/03852
§ 371 (c)(1),
(2), (4) Date: Mar. 30, 2006
PCT Pub. No.: WO2004/087243
PCT Pub. Date: Oct. 14, 2004

(51) Int. Cl.
*A61M 13/00* (2006.01)
*A61M 15/08* (2006.01)
*A61M 15/00* (2006.01)
*A61M 16/00* (2006.01)

(52) U.S. Cl.
USPC ..... 604/58; 128/203.18; 128/203.19; 128/203.22

(58) Field of Classification Search
USPC ..... 604/94.01, 167.05, 205, 234, 54–58, 604/110; 128/203.15, 203.21–203.24
See application file for complete search history.

(56) References Cited

U.S. PATENT DOCUMENTS 3,906,950 A 9/1975 Cocozza
4,013,075 A * 3/1977 Cocozza ..... 128/203.15
4,159,345 A 6/1979 Takeo et al.
4,226,233 A * 10/1980 Kritzer ..... 128/205.13
4,300,545 A 11/1981 Goodnow et al.
4,613,500 A 9/1986 Suzuki et al.
4,889,114 A * 12/1989 Kladders ..... 128/203.15
5,098,907 A 3/1992 Kondo et al.
5,320,094 A 6/1994 Laube et al.
5,419,315 A 5/1995 Rubsamen
5,647,349 A * 7/1997 Ohki et al. ..... 128/203.15
5,672,581 A 9/1997 Rubsamen et al.
5,674,507 A 10/1997 Banker et al.
5,683,361 A * 11/1997 Elk et al. ..... 604/58

(Continued)

FOREIGN PATENT DOCUMENTS

EP 0122036 A1 10/1984
EP 0147755 7/1985

(Continued)

OTHER PUBLICATIONS

European search report dated Jul. 15, 2008 for Application No. 05768543.0.

(Continued)

*Primary Examiner* — Rebecca E Eisenberg
(74) *Attorney, Agent, or Firm* — Wilson, Sonsini, Goodrich & Rosati

(57) ABSTRACT

Improvement for the device to deliver the powdery medicine into nasal cavities in which a capsule setting/detaching part 40 is built drawably in the capsule housing/holding part 30, and cutting blades 60A, 60B are built in both axial ends of the capsule setting/detaching part 40 of the capsule housing/holding part 30 for cutting both axial ends of the capsule thereby perforating the capsule. A medicine capturing/collecting part 32 and a one-way valve 33 are built in a lower portion of the capsule housing/holding part 30, and a pump 50 having an air inlet valve 54 is built in the air flow inlet side thereof. A medicine delivery part 20 is built in the air exit of the capsule housing/holding part 30, a nozzle 22 is installed and medicine in the capsule can be dosed to the nasal cavities of the user by pressing the pump 50.

38 Claims, 7 Drawing Sheets

(56) References Cited

U.S. PATENT DOCUMENTS

| | | | | |
|---|---|---|---|---|
| 5,731,303 | A | 3/1998 | Hsieh | |
| 5,756,483 | A | 5/1998 | Merkus et al. | |
| 5,804,209 | A | 9/1998 | De Ponti et al. | |
| 5,810,004 | A * | 9/1998 | Ohki et al. | 128/203.15 |
| 5,939,100 | A | 8/1999 | Albrechtsen et al. | |
| 5,942,242 | A | 8/1999 | Mizushima et al. | |
| 5,948,749 | A | 9/1999 | Igarashi et al. | |
| 5,958,458 | A | 9/1999 | Norling et al. | |
| 5,989,217 | A | 11/1999 | Ohki et al. | |
| 6,136,295 | A | 10/2000 | Edwards et al. | |
| 6,197,328 | B1 | 3/2001 | Yanagawa | |
| 6,248,363 | B1 | 6/2001 | Patel et al. | |
| 6,273,086 | B1 * | 8/2001 | Ohki et al. | 128/203.21 |
| 6,298,846 | B1 * | 10/2001 | Ohki et al. | 128/203.15 |
| 6,516,795 | B1 * | 2/2003 | Bougamont et al. | 128/200.14 |
| 6,815,424 | B2 | 11/2004 | Vickery et al. | |
| 6,824,080 | B2 | 11/2004 | Matsugi et al. | |
| 6,835,389 | B1 | 12/2004 | Dohi et al. | |
| 6,855,913 | B2 | 2/2005 | Nikodym | |
| 6,906,027 | B2 | 6/2005 | Oki et al. | |
| 7,115,281 | B2 | 10/2006 | Singh et al. | |
| 7,278,982 | B2 | 10/2007 | Tsutsui | |
| 7,306,787 | B2 | 12/2007 | Tarara et al. | |
| 7,353,823 | B2 | 4/2008 | Tsutsui | |
| 7,638,138 | B2 | 12/2009 | Oki et al. | |
| 7,806,117 | B2 | 10/2010 | Tsutsui | |
| 2001/0027301 | A1 | 10/2001 | Lau et al. | |
| 2001/0038824 | A1 | 11/2001 | Horii et al. | |
| 2002/0002172 | A1 | 1/2002 | Bell-Huff et al. | |
| 2002/0012688 | A1 | 1/2002 | Dohi et al. | |
| 2002/0040139 | A1 | 4/2002 | Billotte et al. | |
| 2002/0062829 | A1 | 5/2002 | Ohki et al. | |
| 2003/0199424 | A1 | 10/2003 | Smith et al. | |
| 2004/0063615 | A1 | 4/2004 | Oki et al. | |
| 2004/0076588 | A1 | 4/2004 | Batycky et al. | |
| 2004/0092428 | A1 | 5/2004 | Chen et al. | |
| 2004/0173211 | A1 * | 9/2004 | Kladders et al. | 128/203.15 |
| 2004/0241232 | A1 | 12/2004 | Brown et al. | |
| 2005/0022812 | A1 | 2/2005 | Hrkach | |
| 2005/0042177 | A1 | 2/2005 | Ryde et al. | |
| 2005/0142073 | A1 | 6/2005 | Watts et al. | |
| 2005/0177095 | A1 | 8/2005 | Tsutsui | |
| 2006/0106057 | A1 | 5/2006 | Daniel et al. | |
| 2006/0116657 | A1 | 6/2006 | Schmid | |
| 2006/0216352 | A1 | 9/2006 | Nystrom et al. | |
| 2006/0217658 | A1 | 9/2006 | Tsutsui | |
| 2006/0233715 | A1 | 10/2006 | Oki et al. | |
| 2007/0055200 | A1 | 3/2007 | Gilbert | |
| 2007/0060868 | A1 | 3/2007 | Tsutsui et al. | |
| 2007/0065509 | A1 | 3/2007 | Kanikanti et al. | |
| 2007/0098804 | A1 | 5/2007 | Aronhime et al. | |
| 2007/0178164 | A1 | 8/2007 | Blau | |
| 2007/0184109 | A1 | 8/2007 | Floyd et al. | |
| 2007/0249674 | A1 | 10/2007 | Bolton et al. | |
| 2007/0272763 | A1 | 11/2007 | Dunne et al. | |
| 2008/0029084 | A1 | 2/2008 | Costantino et al. | |
| 2008/0031959 | A1 | 2/2008 | Blondino et al. | |
| 2008/0090841 | A1 | 4/2008 | Johnson et al. | |
| 2008/0127972 | A1 | 6/2008 | Morton | |
| 2008/0260848 | A1 | 10/2008 | Nagata et al. | |
| 2008/0286362 | A1 | 11/2008 | Baran Jr. et al. | |
| 2009/0157037 | A1 | 6/2009 | Iyer et al. | |
| 2009/0169640 | A1 | 7/2009 | Oki et al. | |
| 2010/0178331 | A1 | 7/2010 | Nagata et al. | |
| 2011/0033544 | A1 | 2/2011 | Nagata et al. | |
| 2011/0045088 | A1 | 2/2011 | Tsutsui et al. | |
| 2013/0287852 | A1 | 10/2013 | Oki et al. | |

FOREIGN PATENT DOCUMENTS

| | | | |
|---|---|---|---|
| EP | 0147755 | A2 | 7/1985 |
| EP | 0761248 | A1 | 3/1997 |
| EP | 0943326 | A1 | 9/1999 |
| EP | 1025859 | A1 | 8/2000 |
| EP | 1108423 | A1 | 6/2001 |
| EP | 1454648 | A1 | 9/2004 |
| EP | 1504780 | A1 | 2/2005 |
| EP | 1785145 | A1 | 5/2007 |
| GB | 2395900 | A | 6/2004 |
| JP | 3912469 | | 7/1964 |
| JP | 53127553 | | 11/1978 |
| JP | 54062328 | | 5/1979 |
| JP | 59-34267 | | 2/1984 |
| JP | 59-34267 | A | 2/1984 |
| JP | 59-163313 | A | 9/1984 |
| JP | 60-185564 | | 9/1985 |
| JP | 60-224616 | | 11/1985 |
| JP | 62-42888 | | 9/1987 |
| JP | 63267731 | | 11/1988 |
| JP | 3-29146 | | 3/1991 |
| JP | 5-32560 | | 2/1993 |
| JP | 7-165613 | A | 6/1995 |
| JP | 8-098888 | | 4/1996 |
| JP | 08-206208 | A | 8/1996 |
| JP | 08243164 | | 9/1996 |
| JP | 9-276405 | | 10/1997 |
| JP | 9-291026 | A | 11/1997 |
| JP | 10-59841 | A | 3/1998 |
| JP | 10059841 | | 3/1998 |
| JP | 11/216357 | | 8/1999 |
| JP | 11-322582 | | 11/1999 |
| JP | 2000-229859 | A | 8/2000 |
| JP | 2000-239187 | | 9/2000 |
| JP | 2001-55323 | A | 2/2001 |
| JP | 2002-255795 | A | 9/2002 |
| JP | 2003-154006 | A | 5/2003 |
| JP | 2003-175103 | A | 6/2003 |
| JP | 2003-206227 | A | 7/2003 |
| WO | WO 94/04133 | A1 | 3/1994 |
| WO | WO 95/12399 | A1 | 5/1995 |
| WO | WO 95/34582 | A1 | 12/1995 |
| WO | WO 97/31626 | A1 | 9/1997 |
| WO | WO 98/30207 | A1 | 7/1998 |
| WO | WO 99/16422 | A1 | 4/1999 |
| WO | WO 99/16470 | A1 | 4/1999 |
| WO | WO 99/51205 | A1 | 10/1999 |
| WO | WO 00/12063 | A1 | 3/2000 |
| WO | WO 00/12136 | A1 | 3/2000 |
| WO | WO 00/23023 | A1 | 4/2000 |
| WO | WO 00/38811 | A1 | 7/2000 |
| WO | WO 01/26630 | A1 | 4/2001 |
| WO | WO 01/32125 | A2 | 5/2001 |
| WO | WO 02/32406 | A2 | 4/2002 |
| WO | WO 02/094233 | A1 | 11/2002 |
| WO | WO 03/004048 | A1 | 1/2003 |
| WO | WO 2008/031028 | A2 | 3/2003 |
| WO | WO 03/030872 | A2 | 4/2003 |
| WO | WO 03/077825 | A2 | 9/2003 |
| WO | 03/095008 | | 11/2003 |
| WO | WO 03/095008 | A1 | 11/2003 |
| WO | WO 2004/004922 | A1 | 1/2004 |
| WO | WO 2004/073729 | A1 | 9/2004 |
| WO | WO 2005/013937 | A2 | 2/2005 |
| WO | WO 2005/056008 | A1 | 6/2005 |
| WO | WO 2005/104712 | A2 | 11/2005 |
| WO | WO 2006/016530 | A1 | 2/2006 |
| WO | WO 2006/040680 | A1 | 4/2006 |
| WO | WO 2008/075102 | A1 | 6/2008 |
| WO | WO 2008/078730 | A1 | 7/2008 |
| WO | WO 2008/031028 | A3 | 11/2008 |
| WO | WO 2009/095684 | A1 | 8/2009 |

OTHER PUBLICATIONS

International search report dated May 7, 2003 for PCT Application No. JP2003/001948.

International search report dated Nov. 1, 2005 for PCT Application No. JP2005/014389.

International search report dated Feb. 5, 2008 for PCT Application No. JP2007/074787.

International search report Jun. 8, 2010 for PCT Application No. JP2010/003285.

(56) References Cited

OTHER PUBLICATIONS

Kleinebudde, et al. Influence of degree of polymerization on behavior of cellulose during homogenization and extrusion/spheronization. AAPS Pharmasci 2000, 2(2) Article 21, 1-10.
Rowe, et al (Eds). Handbook of Pharmaceutical Excipients. Pharmaceutical Press. 2003. pp. 108-109.
International search report and written opinion dated Jun. 28, 2011 for PCT Application No. IB2010/02168.
UK combined office action and search report dated Nov. 10, 2010 for Application No. GB1012959.1.
International search report (partial) dated Dec. 21, 2010 for PCT Application No. IB2010/02168.
European search report and opinion dated Dec. 19, 2011 for Application No. 07860016.0.
Office action dated Sep. 28, 2011 for JP Application No. 2006-531575 (in Japanese with English translation).
UK search report dated Sep. 9, 2011 for Application No. GB1012959.1.
U.S. Appl. No. 13/649,515, filed Oct. 11, 2012, Nagata et al.
"Fluorouracil" definition viewed on the National Cancer Institute website at www.cancergov/drugdictionary?cdrid=43130 on May 31, 2012.
Hens, et al., "BMP4 and PTHrP interact to stimulate ductal outgrowth during embryonic mammary development and to inhibit hair follicle induction," Development 2007, 234, pp. 1221-1230.
Merriam-Webster's Collegiate Dictionary, 10th edition, Merriam-Webster Incorporated: Springfield, Massachusetts, 1993, pp. 41.
Advisory action dated Sep. 13, 2013 for U.S Appl. No. 12/848,850.
Hibberd, et al. Immunization strategies for the immunocompromised host: the need for immunoadjuvants. Ann Intern Med. Jun. 15, 1989;110(12):955-6.
Ishikawa, et al. Improved nasal bioavailability of elcatonin by insoluble powder formulation. Int J Pharm. Aug. 14, 2001;224(1-2):105-14.
Office action dated Jan. 13, 2011 for U.S. Appl. No. 12/346,537.
Office action dated Jan. 29, 2008 for U.S. Appl. No. 10/545,764.
Office action dated Mar. 4, 2013 for U.S. Appl. No. 12/848,850.
Office action dated Apr. 20, 2012 for U.S. Appl. No. 12/780,433.
Office action dated May 7, 2013 for U.S. Appl. No. 11/660,131.
Office action dated Jun. 4, 2012 for U.S. Appl. No. 12/521,116.
Office action dated Jun. 25, 2012 for U.S. Appl. No. 12/346,537.
Office action dated Sep. 6, 2011 for U.S. Appl. No. 12/346,537.
Office action dated Sep. 20, 2013 for U.S. Appl. No. 13/827,859.
Office action dated Sep. 24, 2008 for U.S. Appl. No. 10/545,764.
Office action dated Sep. 27, 2010 for U.S. Appl. No. 11/660,131.
Office action dated Oct. 10, 2012 for U.S. Appl. No. 12/780,433.
Office action dated Oct. 15, 2012 for U.S. Appl. No. 12/848,850.
Office action dated Oct. 29, 2009 for U.S. Appl. No. 11/660,131.
Office action dated Nov. 1, 2012 for U.S. Appl. No. 11/660,131.
Office action dated Dec. 5, 2011 for U.S. Appl. No. 12/346,537.
European search report and opinion mailed Dec. 20, 2013 for Application No. 10774745.3.
Component definition, Dictionary.com, accessed Apr. 1, 2014, pp. 1-4.
Labiris, et al. Pulmonary drug delivery. Part I: physiological factors affecting therapeutic effectiveness of aerosolized medications. Br J Clin Pharmacol. Dec. 2003;56(6):588-99.
Office action dated Apr. 8, 2014 for U.S. Appl. No. 13/827,859.
Office action dated Apr. 9, 2014 for U.S. Appl. No. 12/780,433.
Partition Coefficient, Wikipedia, accessed Mar. 31, 2014, pp. 1-8.
Topliss, John. Quantitative Structure-Activity Relationships of Drugs, 1983, pp. 2.
English Language Abstract of JP 9-276405.
English Language Abstract of JP 8-098888.
U.S. Appl. No. 10/512,857, in the name of Tatsu Tsuisui, filed May 13, 2003.
Partial English Language Translation of JP 3-29146.
Partial English Language Translation of JP 59-34267.

* cited by examiner

POWDER MEDICINE APPLICATOR FOR NASAL CAVITY

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

TECHNICAL FIELD

The present invention concerns an optimal device to deliver powdery medicine dosing into the nasal cavity.

A treatment method to deliver a powdery medicine into the nasal cavity of a patient suffering from asthma or nasal allergy has been known generally. In the treatment method, a powdery medicine filled in a capsule is administered into the nasal cavity using a special delivery device. JP-A No. 59-34267 (hereinafter referred to as prior art) has proposed a delivery device used for the treatment. The device of the prior art comprises a cylindrical member having a pump on the air inlet and a concave part in which a capsule is inserted on the air exit of the cylindrical member. A top end part is fitted into the concave part to form a capsule housing part, and an air guide passage having a valve mechanism is formed from the capsule housing part to the pump.

Another valve mechanism is provided to the other side of the pump, and air is supplied to the capsule housing part through the air guide passage having a valve mechanism upon pressing of the pump, and external air is sucked into the pump through the another valve upon removal of the pump pressure.

Further, the cylindrical member has, at its top end, a cap fitted to the top end and a needle is extended axially in the cap so as to perforate both axial ends of the capsule by engaging the cap in a state of fitting the concave part of the cylindrical member and the top end having an opening.

In the prior art device of the constitution described above, after inserting the capsule filled with a powdery medicine into the concave part of the cylindrical member, the capsule is inserted and fixed in the capsule housing portion by fitting the top end. Then a cap is fitted to the top end made of a hard resin to perforate at both axial top ends of the capsule by a needle built inside the cap and guided to the top end.

Then, when the medicine is dosed, a user detaches the cap from the cylindrical member and inserts the top end into one of the nasal nostril and presses the pump. Then, when the pump is pressed, air from the pump flows through the air guide passage into the capsule to deliver the medicine in the capsule to the nasal cavity of the user. Further, by repeating the operations for both nasal cavities, the medicine is dosed to both of the nasal cavities.

In the device of the prior art described above, after inserting the capsule in the cylindrical member, the top end is fitted detachably to the cylindrical member and then a cap is detachably provided to the cylindrical member. However, such operations to deliver are troublesome and it may be a worry that the user should forget such operations. Further, in a case where the top end or the cap is missed, it can no more be used as the delivery device.

Further, when the powdery medicine is dropped in the course of operations from perforation to dosing operation in the pump passing through the valve mechanism in the air guide passage, it will bring about a problem that the amount of the medicine is reduced, the medicine can not be delivered at an adequate dose for the user and the medicine dropped in the pump has to be cleaned.

Further, upon dosing of the medicine, the user inserts the top end into the nasal nostril. However, since the top end is made of a rigid resin, it may be a worry of injuring the nasal nostril upon insertion. Further, since the top end does not smoothly fitted to the shape of the user's nostril, this hinders application of medicine to the nasal cavity making it impossible for efficient dosing.

The present invention intends to overcome such problems.

DISCLOSURE OF THE INVENTION

The present invention of claim 1 for solving the problems described above comprises a capsule housing/holding part for housing and holding a capsule filled with a powdery medicine, a pump installed in the capsule housing/holding part for supplying dosing air to the capsule housing/holding part, a medicine delivery part with a top end which may be optionally branched into two ways for delivering the medicine in the capsule loaded into the capsule housing/holding part from the pump to the user's nasal cavity by air supplied through an air flow passage formed in the capsule housing/holding part, a capsule setting/detaching part built drawably in the capsule housing/holding part so as to be movable in the lateral direction relative to the axial direction of the capsule for setting and detaching the capsule thereby perforating at both axial ends of the capsule, and cutting blades built laterally relative to the axial direction of the capsule in the capsule housing/holding part for perforating at both axial ends of the capsule.

The invention of claim 2 comprises a medicine capturing/collecting part having a specific structure of an air flow passage for capturing and collecting a powdery medicine dropping and flowing backwardly from the capsule after perforation so as not to flow the medicine backwardly and capable of dosing the thus captured and collected powdery medicine by the pump actuation, and a one-way valve the opening pressure of which is controlled by a spring.

Further, the invention of claim 3 comprises the nozzle for the medicine spray part constituted with a flexible tube for insertion while conforming the shape of the user's nasal nostril for dosing when the user applies the powdery medicine to the nasal cavity.

More specifically, according to the delivery device for the powdery medicine of claim 1 provided by the present invention, a capsule is placed in the capsule setting/detaching part built drawably so as to move in the lateral direction relative the axial direction of the capsule in the capsule housing/holding part and cutting blades built laterally to the axial direction of the capsule in the capsule housing/holding part perforate at both axial ends of the capsule.

Further, air is supplied from the pump upon dosing and the air flows into the perforated capsule to deliver and dose the medicine in the capsule through the medicine passage in the medicine delivery part from the nozzle to the user's nasal cavity.

Further, in the invention according to claim 2, since the medicine capturing/collecting part, and the one-way valve the opening pressure of which is controlled by the spring are built in the air flow passage between the capsule housing/holding part and the pump, they capture and collect the medicine falling and flowing backwardly from the capsule to the pump upon perforation of the capsule and can prevent falling and backward flow to the pump.

Further, upon dosing, the one-way valve is opened by the flow under pressure of air from the pump to deliver and dose the captured and collected medicine together with the medicine in the capsule by way of the capsule housing/holding part and the medicine delivery part from the nozzle to the user's nasal cavity.

Further according to the invention described more specifically in claim 3, the user inserts the nozzle of the medicine delivery part into the nasal nostril upon dosing the medicine to the nasal cavity. Since the nozzle is made of a flexible tube, it can be inserted conforming the user's nasal nostril.

Figure 1:
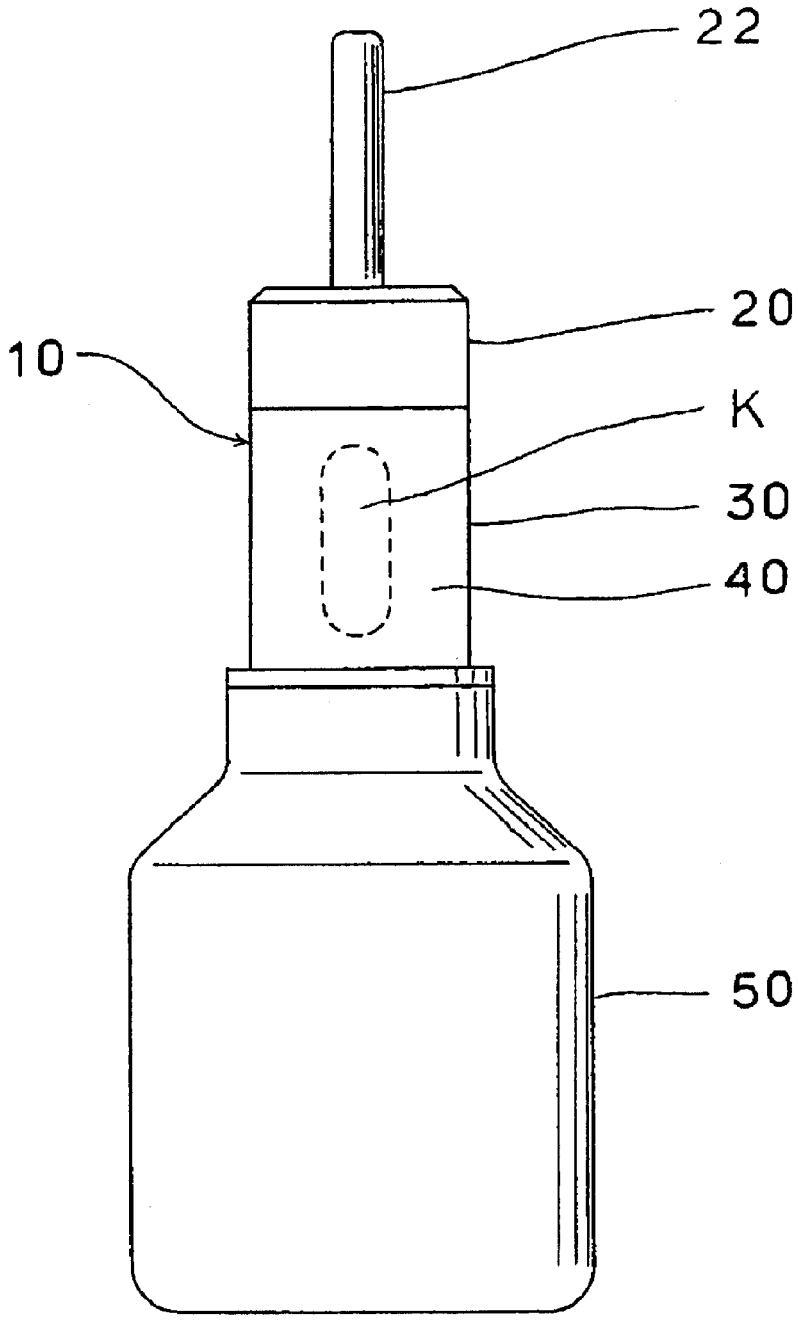
FIG. 1 is a side elevational view illustrating an embodiment of a powdery medicine delivery device according to the present invention.

Each of the references has the following meanings

10 device to deliver the powdery medicine into the nasal cavity
20 medicine delivery part
21 medicine passage
22, 22A, 22B nozzle
30 capsule housing/holding part
31 air flow passage
32 medicine capturing/collecting part
33 one-way valve
34 spring
35 air flow inlet
36 abutment surface
37 protrusion
38 lower portion of the capsule housing/holding part
40 capsule setting/detaching part
41 capsule attaching/detaching concave part
42A, 42B capsule cut end discharge part
44 drawing end
45 protrusion for capsule setting/detaching part
46 end face for capsule setting/detaching part
50 pump
51 attaching part
52 bottom
53 pressing part
54 air intake valve
55 air intake valve
56 intake valve body
60A, 60B cutting blade
K capsule
KA, KB capsule end

BEST MODE FOR PRACTICING THE INVENTION

The present invention is to be described by way of embodiments with reference to the drawings. An embodiment of the present invention is to be described with reference to FIG. 1 to FIG. 7.

Figure 2:
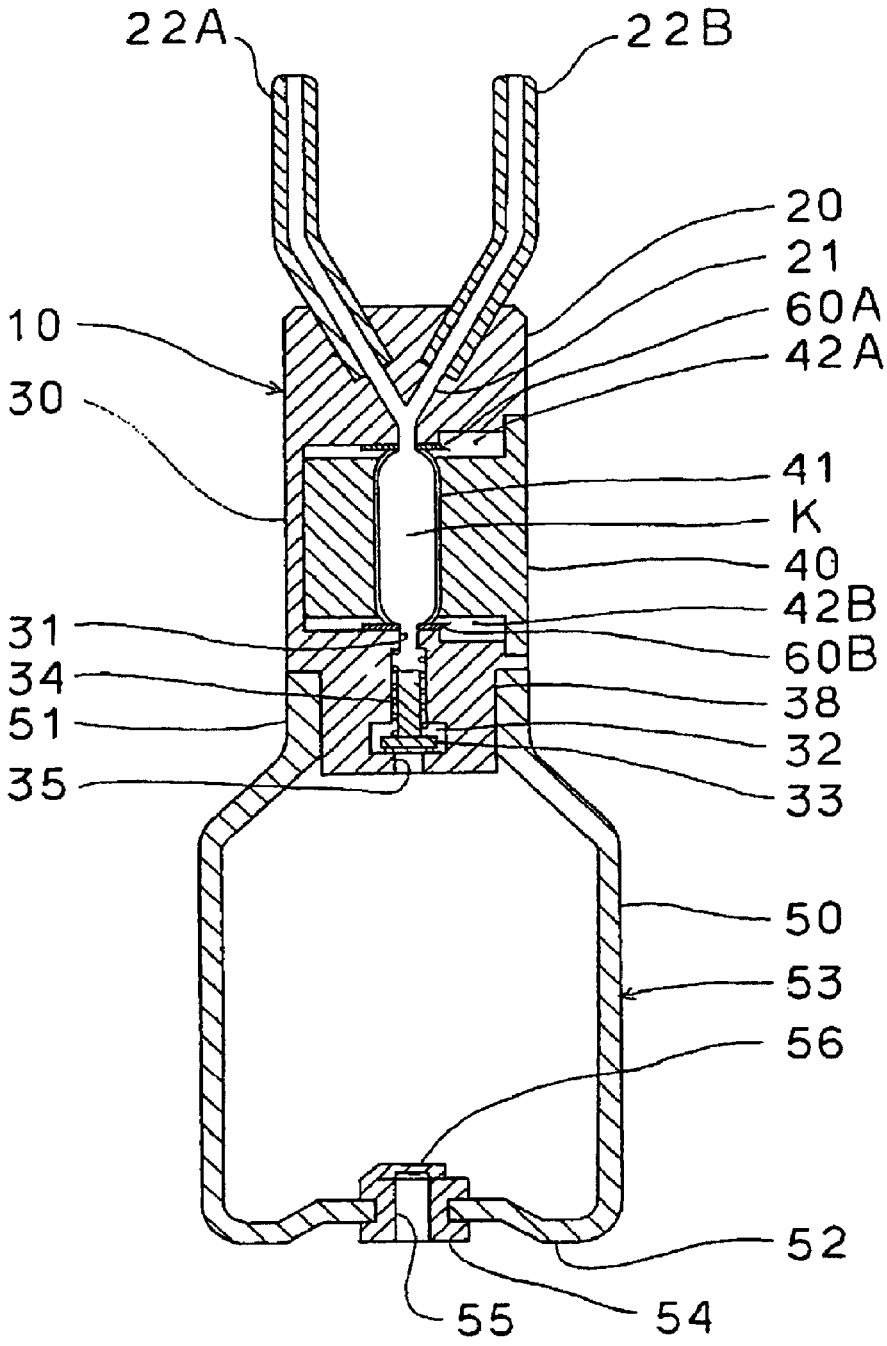
FIG. 2 is a cross sectional view illustrating an embodiment of a powdery medicine delivery device according to the present invention.

FIG. 1 is a side elevational view of an embodiment of a device to deliver the powdery medicine into the nasal cavity according to the present invention and FIG. 2 is a cross sectional side elevational view of a device to deliver the powdery medicine into the nasal cavity shown in the embodiment.

In the drawings, a powdery medicine delivery device 10 for nasal cavity comprises, generally, a capsule housing/holding part 30 for housing and holding a capsule K together with a medicine delivery part 20, a capsule setting/detaching part 40 built drawably in the capsule housing/holding part 40 and a pump 50 built in the air inlet side of the capsule housing/holding part 30 for supplying air to the capsule, and cutting blades 60a, 60b situated at both axial ends of the capsule K of the capsule setting/detaching part 40 of the capsule housing/holding part 30 for perforating holes at both axial ends of the capsule K by setting/detaching operation of the capsule setting/detaching part 40.

In the medicine delivery part 20 of this embodiment, a medicine passage 21 is built in an upper part (air exit side) with respect to the axial direction of the capsule K of the capsule housing/holding part 30, and nozzles 22A and 22B made of flexible tubes are formed to the top end of the medicine passage 21.

An air flow passage 31 of the capsule housing/holding part 30 axially below the capsule K (air inlet side) includes a medicine capturing/collecting part 32 for capturing and collecting the powdery medicine falling and flowing backwardly from the capsule K, and a one-way valve 30 also preventing falling and backward flowing of the powdery medicine from the capsule K to the pump 50. The one-way valve 33 is adapted to prevent back flow of air such that it opens when the pressure of air from the pump 50 reaches at or higher than a prescribed pressure and closes the air flow inlet 35 when the pressure of air from the pump 50 is lower than the prescribed pressure.

The capsule setting/detaching part 40 has a capsule attaching/detaching recess 41 at a position of attaching or detaching the capsule K, such that it can be set and detached drawably in the lateral direction with respect to the axial direction of the capsule K to the capsule housing/holding part 30 and a drawing end 44 of the capsule setting/detaching part 40 is regulated by the abutment of the detaching end 44 to the protrusion 37 built in the capsule housing/holding part 30.

Further, when the capsule setting/detaching part 40 is pushed into the capsule housing/holding part 30, the inlet end is regulated by the abutment of a setting/detaching protrusion 45 of the capsule setting/detaching part 40 against the abutment face 36 of the capsule housing/holding part 30.

The pump 50 is comprised of a resilient rubber material into a bottomed cylindrical shape having an attaching part 51, a bottom 52 and a pressing part 53 at the circumferential surface. The attaching part 51 is mounted sealingly to the cylindrical outer circumferential surface of the capsule housing/holding lower part 38 of the capsule housing/holding part 30, and an air inlet valve 54 is attached to a central portion of the bottom 52.

The air intake valve 54 produced using a resilient rubber material is comprised of an air inlet form 55 and an inlet valve body 56. The valve is closed when the pump 50 is pressed, while the valve is opened upon restoration of the pump 50 after pressing to supply external air to the pump 50.

The powdery medicine delivery device 10 for nasal cavity according to this embodiment has been constituted as described above.

Figure 3:
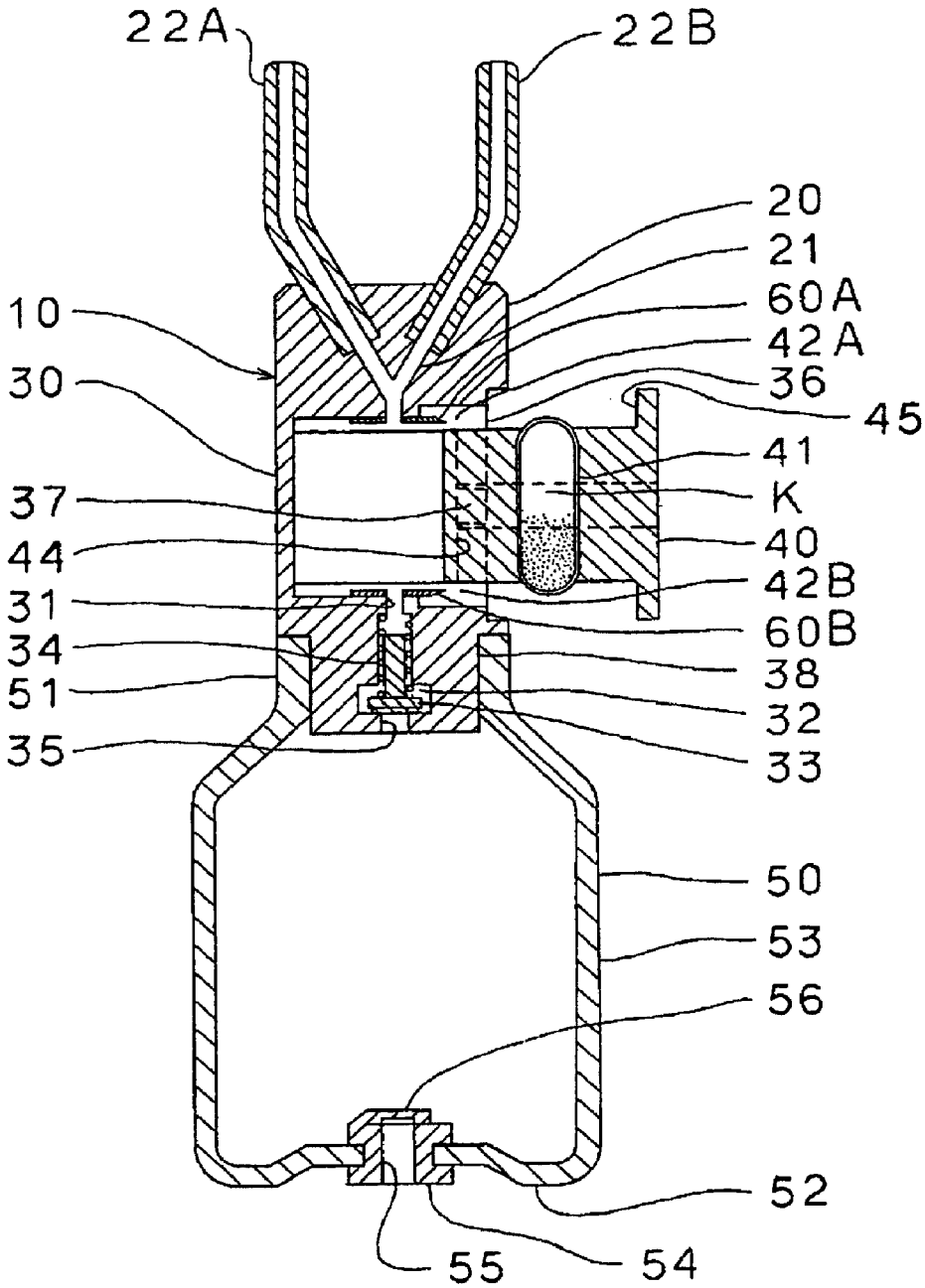
FIG. 3 is a view showing a state of drawing out a capsule setting/detaching part and placing a capsule therein in FIG. 2.
Figure 4:
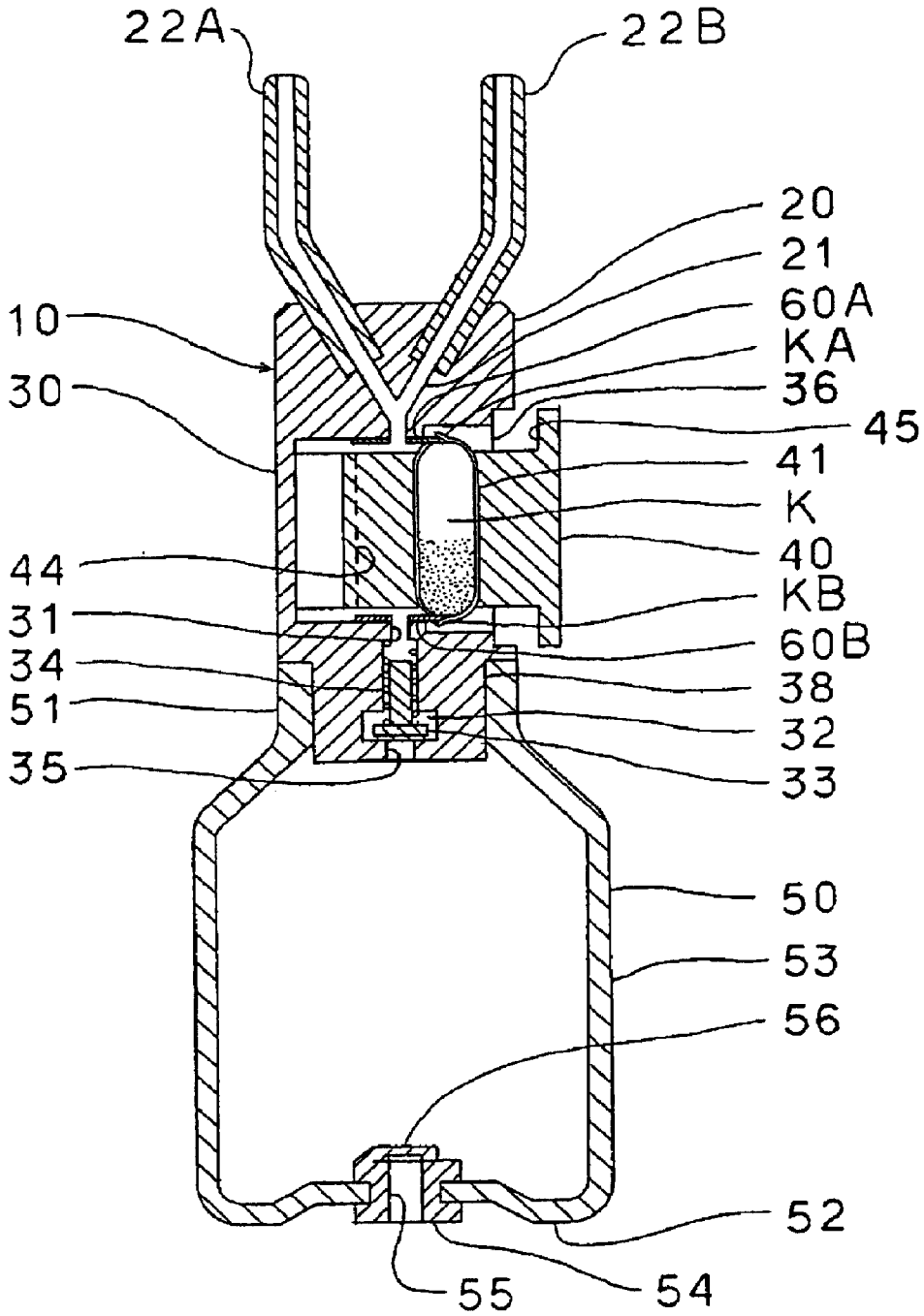
FIG. 4 is a cross sectional side elevational view showing a state in which cutting blades are cutting a capsule end in the course where the capsule setting/detaching part with the capsule placed therein is inserted into a capsule housing/holding part.
Figure 5:
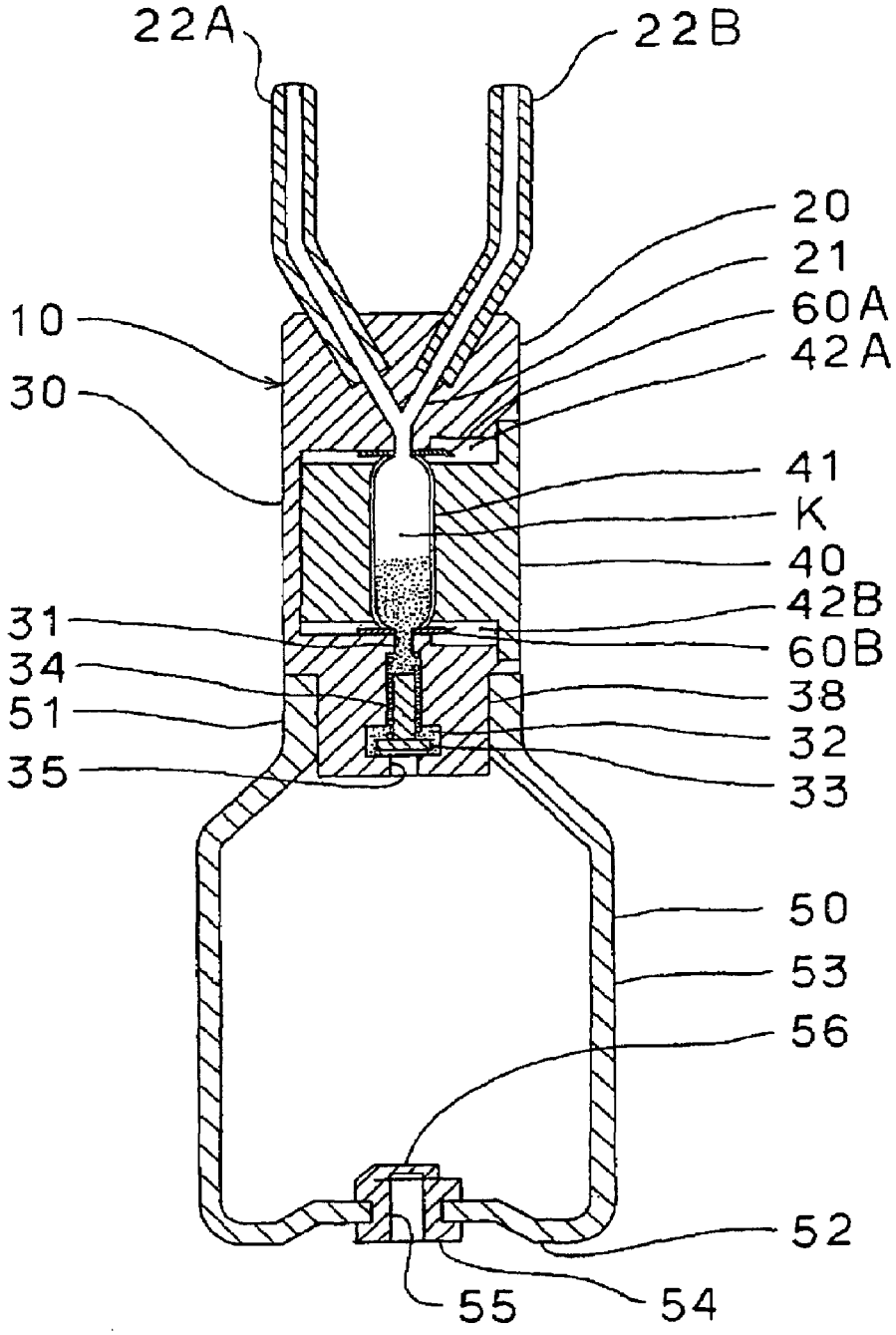
FIG. 5 is a cross sectional view showing a state in which the capsule end is cut off by cutting blades, and the medicine in the capsule upon completion of perforation is falling and flowing backwardly to the pump in FIG. 2.

Then, description is to be made to an operation upon perforation of the capsule with reference to FIG. 3 to FIG. 5.

At first, as shown in FIG. 3, the capsule K is placed in the capsule attaching/detaching concave 41 of the capsule setting/detaching part 40 and the capsule setting/attaching end face 46 of the capsule setting/detaching part 40 is pressed so as to intrude the capsule setting/detaching part 40 into the capsule housing/holding part 30.

Then, as shown in FIG. 4, as the capsule K placed in the capsule setting/detaching concave 41 of the capsule setting/detaching part 40 intrudes into the capsule housing/holding part 30, the cutting blades 60A, 60B built laterally at both axial ends of the capsule K in the capsule housing/holding part 30 cut off both axial ends KA, KB of the capsule K, thereby perforating both ends of the capsule K.

Further, when the capsule setting/detaching end face 46 of the capsule setting/detaching part 40 is pushed to abut the setting/detaching protrusion 45 against the abutment surface 36 of the capsule housing/holding part 30, the capsule K that was already perforated with holes at both axial ends pass completely through to the medicine passage 21 of the medicine delivery part 20 and the air flow channel 31 of the capsule housing/holding part 30 to be in a state ready for dosing the medicine.

In this case, as shown in FIG. 5, the medicine in the capsule K perforated at both axial ends thereof falls toward to the air flow passage 31. Since the one-way valve 33 is closed, the medicine is captured and collected in the medicine capturing/collecting part 32.

As described above, upon perforation in the device 10 to deliver the powdery medicine into the nasal cavity in this embodiment, holes are easily perforated at both axial ends of the capsule K only by the operation of housing the capsule K in the device 10 to deliver the powdery medicine into the nasal cavity and the medicine falling and flowing backwardly after perforation is reliably captured by the one-way valve 33 and the medicine capturing/collecting part 22.

Then, operation upon dosing the medicine to the user after perforation to the capsule K is to be described with reference to FIG. 6.

Figure 6:
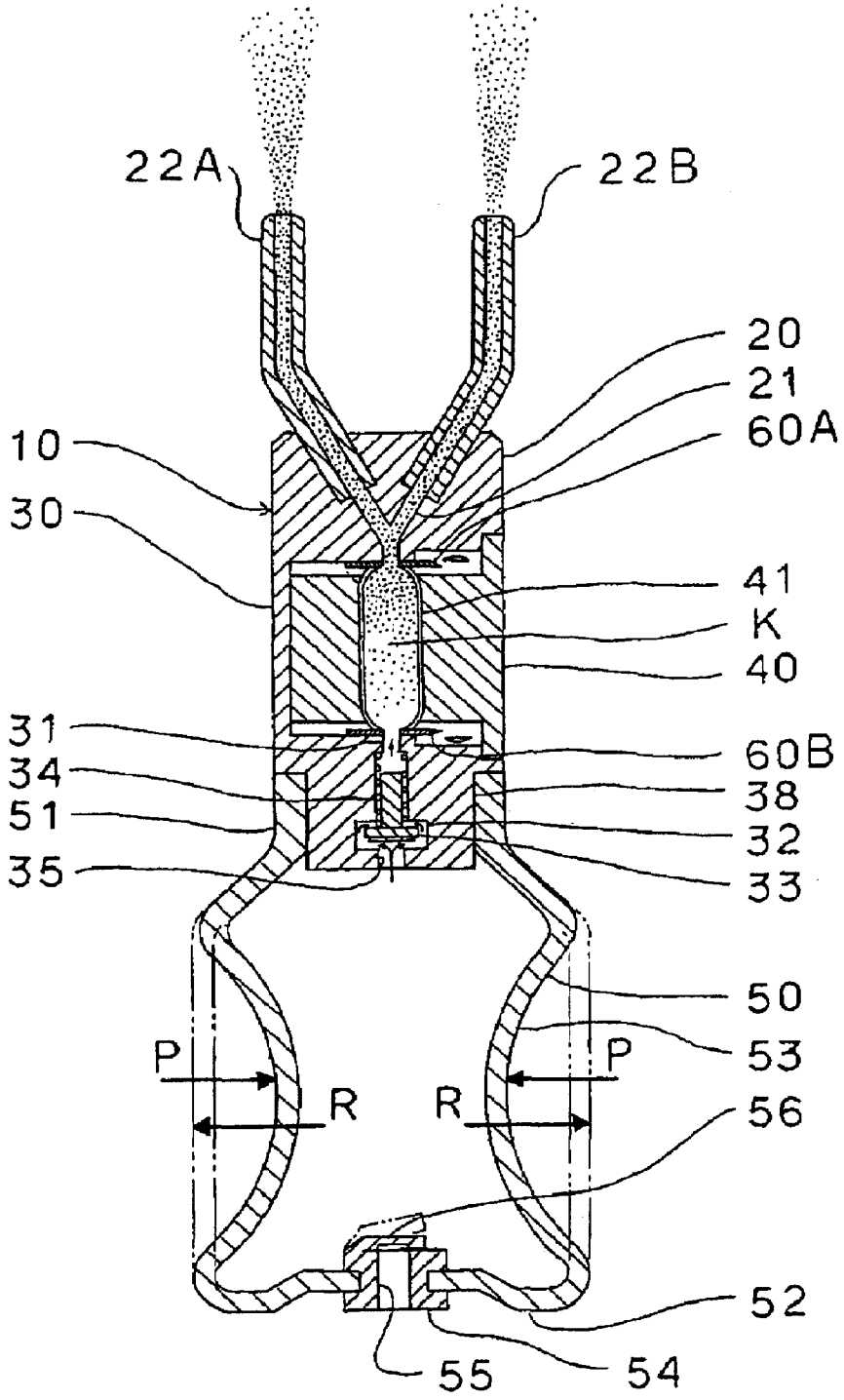
FIG. 6 is a cross sectional view in a state where the medicine in the capsule is under delivery and dosing by pressing the pump.

At first, when the nozzles 22A, 22B of the medicine delivery part 20 are inserted into nasal nostril of a user and the pressing part 53 of the pump 50 is pressed in the direction of an arrow P as shown in FIG. 6, the pressure of air loaded on the one-half way valve 33 increases and, when it reaches to a predetermined pressure, the one-way valve 33 is opened in which air is supplied from the pump 50 through the one-way valve 33, the medicine capturing/collecting part 32 and the air flow channel 31 to the capsule K.

Thus, air from the pump 50 flows from the inside of the capsule K through the medicine passage 21 and the nozzles 22A, 22B to the nasal cavities of the user.

In this process, the medicine in the capsule K is agitated by air flowing inside the capsule K and is delivered and dosed together with air to the nasal cavities of the user.

Further, the medicine that was captured and collected in the medicine capturing/collecting part 32 upon perforation and exists in the medicine capturing/collecting part 32 and in the air flow passage 31 is delivered by air from the pump 50, and is delivered and dosed together with the medicine in the capsule K to the nasal cavities of the user. As a result, a prescribed amount of the medicine filled in the capsule K can be reliably delivered and dosed to the user's nasal cavities.

Further, just before the completion of pressing to the pump 50, pressure of air loaded on the one-way valve 33 is weakened and when it becomes lower than the prescribed pressure to open the one-way valve 33, the one-way valve is closed. Just before the closure of the one-way valve 33, air still flows from the pump 50 to the capsule K. Accordingly, the medicine in the capsule K, the air flow passage 31, and the medicine capturing/collecting part 32 does not fall and flow backwardly to the pump 50 and falling and backward flow of the medicine to the pump 50 can be prevented reliably.

Further, when the pressing to the pump 50 is completed and the pressure is removed, the pressing part 53 of the pump 50 having the rubber resiliency restores in the direction shown by an arrow R to cause a negative pressure in the pump 50, so that the intake valve body 56 of the air intake valve 54 is opened by the pressure of the external air and air flows into the pump 50 from the outside by way of the air intake hole 55 to restore the pressing portion of the pump 50 to an original state as shown by chain double-dashed lines.

In the device 10 to deliver the powdery medicine into the nasal cavity in this embodiment, when the capsule K is placed in the capsule attaching/detaching concave 41 of the capsule setting/detaching part 40 and as the capsule setting/detaching part 40 intrudes in the capsule housing/holding part 30, the cutting blades 60A, 60B situated laterally at both axial ends of the capsule K to the capsule housing/holding part 30 cut off both axial end portions KA, KB of the capsule K to perforate both axial ends of the capsule K. That is, containment of the capsule K and perforation thereof can be conducted with an extremely simple operation consisting only of the operation of housing the capsule K in the device 10 to deliver the powdery medicine into the nasal cavity. In addition, there is no worry of missing the cap for perforation or the top end which was provided as a separate member in the prior art and, further, there is no worry of forgetting the perforating operation which would lead to the dosing failure of the medicine. The capsule can be perforated reliably to ready for dosing the medicine.

Further, the capsule housing/holding part 30 is comprised of the medicine capturing/collecting part 31 for capturing and collecting the powdery medicine falling and flowing backwardly from the capsule K, and the one-way valve 33 also for preventing the falling and backward flowing of the powdery medicine from the capsule K. The one-way valve 33 is adapted such that it opens when the pressure of air from the pump 50 reaches a predetermined pressure, whereas the air flow inlet 35 is closed by the spring 34 when the pressure of air from the pump 50 is lower than the predetermined pressure thereby reliably preventing backward flow of air or medicine. Accordingly, the medicine captured and collected by the medicine capturing/collecting part 32 of the air flow passage 31 and exists therein upon perforation can be delivered and dosed to the user's nasal cavities together with the medicine in the capsule K when the air pressure in the pump 50 increases above the predetermined pressure to open the one-way valve 33. Accordingly, since this can overcome the problem that the medicine can not be delivered at an adequate dose by the falling of the medicine to the pump from the capsule after the perforation, or a problem that the pump has to be cleaned as in the prior art, a predetermined amount of the medicine filled in the capsule K can reliably be delivered and dosed to the nasal cavities of the user.

Further, in the medicine delivery part 20, the medicine passage 21 is built and nozzles 22A, 22B comprising flexible tubes are formed to the top end of the medicine passage 21 and they can be inserted for dosing while conforming the user's nasal nostril upon dosing. As a result, there is neither a worry of injuring the nasal nostril of the user by the insertion of the top ends formed of a rigid resin into the nasal nostril nor a worry that dosing to the nasal cavities is inhibited due to inconformity with the shape of the user's nasal nostril making it impossible for efficient dosing as in the prior art, but efficient dosing can be conducted efficiently in this embodiment while conforming the shape of the user's nasal cavities.

Figure 7:
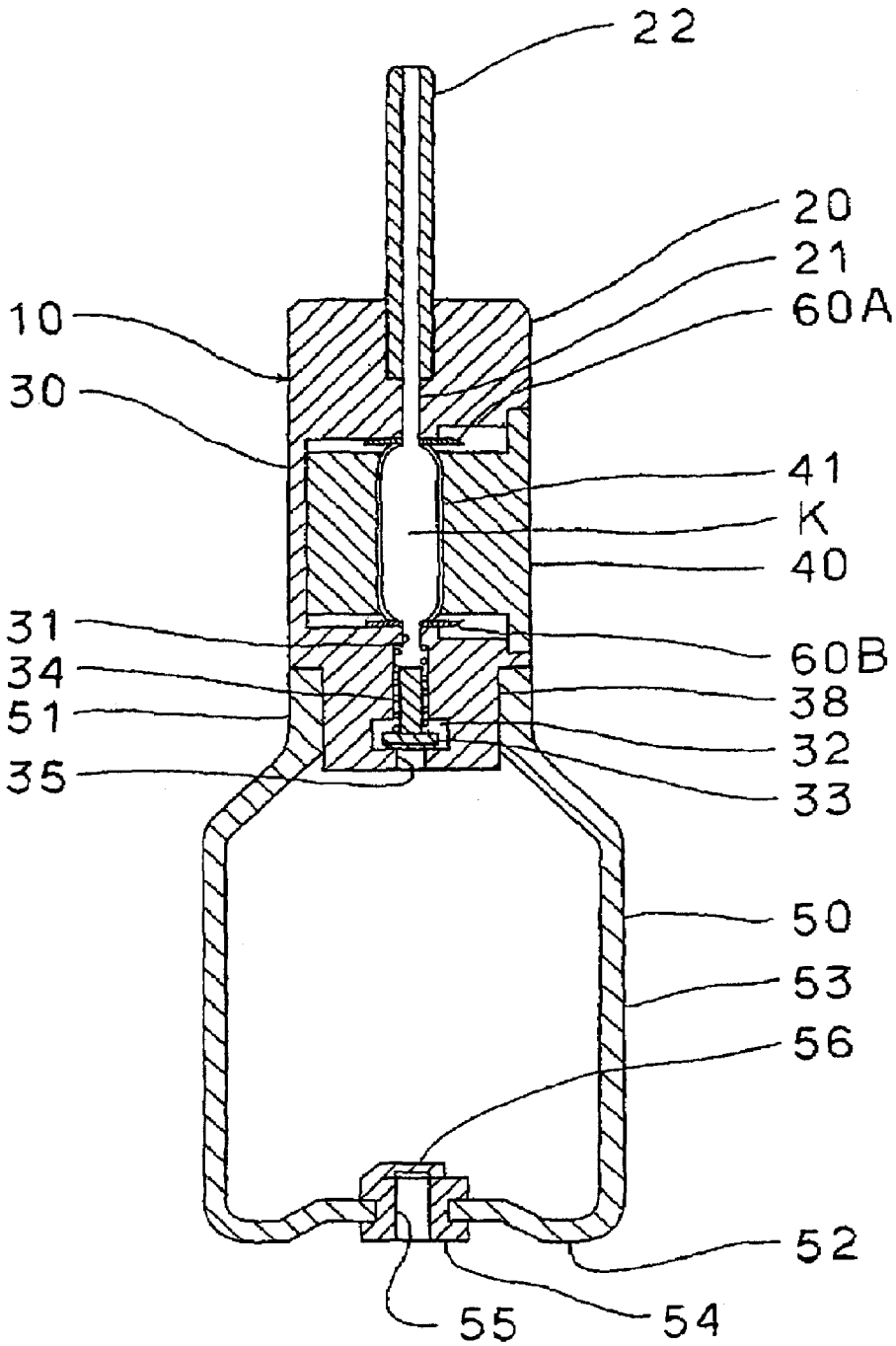
FIG. 7 is a cross sectional view showing another embodiment of a powdery medicine delivery device of the invention.

FIG. 7 is a cross sectional view of a device to deliver the powdery medicine into the nasal cavity according to another embodiment of the present invention (reference numerals in the drawing have same meanings as those in the previous embodiment). This modified embodiment is different from the previous embodiment only in that the nozzle 22 formed of a flexible tube at the top end of the medicine passage 21 comprises a single nozzle in the medicine delivery part 20, and operation upon perforation to the capsule K and the operation upon dosing the medicine to the user after perforation are quite identical with those of the previous embodiment.

INDUSTRIAL APPLICABILITY

As has been described above, according to the invention of claim 1, when the capsule is placed in the capsule detaching/attaching concave part of the capsule setting/detaching part and as a capsule setting/detaching part intrudes into the capsule housing/holding part, the cutting blades situated laterally to the capsule housing/holding part at both axial ends of the capsule cut off both axial ends of the capsule thereby enabling to perforate at both axial ends of the capsule. Subsequently, air is supplied from the pump to the capsule in the capsule housing/holding part to dose the medicine in the capsule together with air from the medicine passage of the medicine delivery part by way of the nozzle to the nasal cavities of the user, so that the operations up to the perforation to the capsule can be conducted only by the operation of housing the capsule into the device to deliver the powdery medicine into the nasal cavity. The present invention can conduct perforation to the capsule reliably by an extremely simple operation without the capsule perforating operation which tends to be forgotten and with no worry of missing separate members such as a cap having a perforating needle or a top end in the prior art, and can perforate the capsule reliably with an extremely simple operation.

Further, according to the invention of claim 2, since the device comprises the air flow passage and the medicine capturing/collecting part having a passage shape for capturing and collecting the medicine dropping and flowing backwardly from the capsule after perforation thereby preventing the medicine from falling into the pump and capable of dosing the captured and collected medicine together with the medicine in the capsule by the operation of the pump, and one-way valve controlled to a predetermined opening pressure by the spring are built between the capsule housing/holding part and the pump, the falling and backwardly flowing medicine upon perforation is delivered and dosed to the nasal cavities of the user together with the medicine in the capsule by way of the capsule housing/holding part and the medicine delivery part, and a predetermined amount of the medicine filled in the capsule can reliably be delivered and dosed to the nasal cavities of the user. Further, since the medicine does not drop at all to the pump, cleaning operation for the pump can be saved.

Further according to the invention described in claim 3, since the nozzle of the medicine delivery part is formed of a flexible tubes, it can be inserted smoothly while conforming the shape of the user's nasal nostril upon inserting the nozzle into the nasal nostril by the user, efficient dosing can be conducted safely while being conformed with the shape of the user's nasal nostril.

The invention claimed is:

1. A device to deliver *a* powdery medicine into [the] *a* nasal cavity, comprising:

a capsule housing/holding part for housing and holding a capsule filled with a powdery medicine, a pump installed in the capsule housing/holding part for supplying dosing air to the capsule housing/holding part, a medicine delivery part with one or branched top end installed in the capsule housing/holding part for delivering and dosing the *powdery* medicine in the capsule of the capsule housing/holding part by air supplied by way of an air flow passage built in the capsule housing/holding part from the pump to the nasal cavity of a user, a capsule selling/detaching part built in the capsule housing/holding part so as to move the capsule in a lateral direction relative to an axial direction of the capsule for setting and detaching a capsule and for perforating both axial ends of the capsule, and cutting blades built in the capsule housing/holding part so as to be movable laterally with respect to an axial direction of the capsule for perforating both axial ends of the capsule, wherein a medicine capturing/collecting part having an air flow passage shape for capturing and collecting the powdery medicine falling and flowing backwardly from the capsule after perforation and not causing them to flow backwardly to the pump, and capable of dosing the captured and collected powdery medicine by the operation of the pump, and a one-way valve the opening pressure of which is controlled by a spring are built in the air flow passage.

2. The device according to claim 1, further comprising a nozzle of the medicine delivery part composed of a flexible tube such that it can be inserted for dosing while conforming [the] *a* nasal nostril of a user when the powdery medicine is dosed to the nasal cavities of the user.

3. The device according to claim 1 wherein the medicine delivery part has a top end branched into two ways.

4. A device to deliver *a* powdery medicine into [the] *a* nasal cavity, comprising:

a capsule housing/holding part for housing and holding a capsule filled with a powdery medicine, a pump *comprising an air intake valve and* installed in the capsule housing/holding part for supplying dosing air to the capsule housing/holding part, a medicine delivery part with one or branched top end installed in the capsule housing/holding part for delivering and dosing the *powdery* medicine in the capsule of the capsule housing/holding part by air supplied by way of an air flow passage built in the capsule housing/holding part from the pump to the nasal cavity of a user, a capsule setting/detaching part built in the capsule housing/holding part so as to move the capsule in a lateral direction relative to an axial direction of the capsule for setting and detaching a capsule and for perforating both axial ends of the capsule, and cutting blades built in the capsule housing/holding part so as to be movable laterally with respect to an axial direction of the capsule for perforating both axial ends of the capsule, wherein a medicine capturing/collecting part having an air flow passage shape for capturing and collecting the powdery medicine falling and flowing backwardly from the capsule after perforation and not causing them to flow backwardly to the pump, and capable of dosing the captured and collected powdery medicine by the operation of the pump, and a one-way valve the opening pressure of which is controlled by a spring are built in the air flow passage, *and* wherein the medicine delivery part has a top end branched into two ways.

5. The device according to claim 2, wherein the medicine delivery part has a top end branched into two ways.

6. The device according to claim 4, further comprising a nozzle of the medicine delivery part composed of a flexible tube such that it can be inserted for dosing while conforming [the] *a* nasal nostril of a user when the powdery medicine is dosed to the nasal cavities of the user.

*7. A device to deliver a powdery medicine, the device comprising:*

*a) a capsule housing adapted to receive a capsule filled with the powdery medicine having an upstream end and a downstream end;*

*b) a capsule setting/detaching part movably in communication with the capsule housing adapted to simultaneously load and perforate the capsule;*

*c) a pump; and*

*d) a medicine capturing/collecting part having:*

*an air flow passage shape for capturing and collecting the powdery medicine falling and flowing backwardly from the capsule after perforation and not causing them to flow backwardly to the pump, and capable of dosing the captured and collected powdery medicine by the operation of the pump, and*

*a one-way valve the opening pressure of which is controlled by a spring built in the air flow passage.*

*8. The device of claim 7, wherein the capsule setting/detaching part is adapted to move in a lateral direction relative to an axial direction of the capsule.*

*9. The device of claim 7, wherein the capsule setting/detaching part comprises a capsule attaching/detaching recess for holding the capsule.*

*10. The device of claim 7, wherein the capsule setting/detaching part has an interior end and an exterior end further comprising an interior end abutment adapted to prevent the complete withdrawal of the capsule setting/detaching part from the capsule housing when the capsule setting/detaching part is moved laterally away from the capsule housing.*

*11. The device of claim 7, wherein the capsule setting/detaching part is adapted to regulate the insertion depth of the capsule attaching/detaching recess into the capsule housing when the capsule setting/detaching part is moved laterally towards the capsule housing.*

*12. The device of claim 11, wherein the depth of insertion of the capsule attaching/detaching recess into the capsule housing when the capsule setting/detaching part is moved laterally towards the capsule housing is regulated by the position of the capsule attaching/detaching recess within the capsule/setting detaching part.*

*13. The device of claim 7, wherein the capsule setting/detaching part has an interior end and an exterior end further comprising an exterior end protrusion adapted to regulate the insertion depth of the capsule setting/detaching part into the capsule housing when the capsule setting/detaching part is moved laterally towards the capsule housing.*

*14. The device of claim 12 or 13, wherein the capsule housing is adapted to perforate the capsule before the setting/detaching protrusion of the setting/detaching part abuts the capsule housing/holding part.*

*15. The device of claim 13, wherein the device is adapted so that once the protrusion of the setting/detaching part abuts the capsule housing/holding part, the device is in a ready state for dosing the powdery medicine.*

*16. The device of claim 7, wherein the capsule housing further comprises one or more cutting blades adapted to perforate at least one axial end of the capsule.*

*17. The device of claim 16, wherein the one or more cutting blades are situated lateral to the axial direction of the capsule.*

*18. The device of claim 7, further comprising a medicine delivery part adapted for delivering the powdery medicine to a user having an upstream end and a downstream end.*

*19. The device of claim 18, further comprising one or more nozzles coupled to downstream end of the medicine delivery part.*

*20. The device of claim 19, wherein the one or more nozzles are flexible.*

*21. The device of claim 19, wherein the one or more nozzles conform to a user's nostril.*

*22. The device of claim 7, wherein the pump is adapted to supply dosing air to disperse the powdery medicine, and coupled to the upstream end of the capsule housing and the one-way valve in communication with the capsule housing.*

*23. The device of claim 22, wherein the pump is adapted so as not to need cleaning between uses.*

*24. The device of claim 22, wherein the pump further comprises an air intake valve.*

*25. The device of claim 22, wherein the pump further comprises a deformable volume adapted to be engaged by a user.*

*26. The device of claim 7 or 22, wherein the one-way valve comprises an upstream end and a downstream end, wherein the downstream end is coupled to the upstream end of the capsule housing.*

*27. The device of claim 7 or 22, wherein the upstream end of the one-way valve is coupled to the pump.*

*28. The device of claim 27, wherein the one-way valve is adapted to open when air from the pump reaches a predetermined pressure.*

*29. The device of claim 7 or 22, wherein the one-way valve is adapted to capture medicine that falls upstream from a perforated capsule.*

*30. The device of claim 29, wherein the device is adapted to deliver the captured medicine to the user.*

*31. The device of claim 29, wherein the one-way valve is further adapted to prevent the upstream flow of medicine into the pump.*

*32. The device of claim 7, wherein a portion of the air flow passage configured to capture the powdery medicine prevents backward flow of the powdery medicine to the pump.*

*33. The device of claim 7, wherein the device is capable of dosing the captured powdery medicine.*

*34. A method for delivering a powdery medicine, the method comprising:*

*loading a capsule containing the powdery medicine into a delivery device comprising a nozzle, a capsule housing, a capsule setting/detaching part, a pump, and a medicine capturing/collecting part having:*

*an air flow passage shape for capturing and collecting the powdery medicine falling and flowing backwardly from the capsule after perforation and not causing them to flow backwardly to the pump, and capable of dosing the captured and collected powdery medicine by the operation of the pump, and*

*a one-way valve the opening pressure of which is controlled by a spring built in the air flow passage,*

*wherein the loading step simultaneously sets the capsule into the delivery device and perforates the capsule;*

*positioning at least a portion of the nozzle of the delivery device into a nostril of a user; and*

*activating the pump, whereby the powder medicine is delivered to the user.*

*35. The method of claim 34, wherein perforation of the capsule occurs at the axial ends of the capsule.*

*36. The method of claim 34, wherein perforation of the capsule is by cutting blades.*

*37. The method of claim 36, wherein the cutting blades are built into the capsule housing.*

*38. The method of claim 34, wherein the step of activating the pump comprises squeezing the pump.*

* * * * *

UNITED STATES PATENT AND TRADEMARK OFFICE

CERTIFICATE OF CORRECTION

PATENT NO. : RE45,404 E
APPLICATION NO. : 12/576219
DATED : March 3, 2015
INVENTOR(S) : Tsutsui It is certified that error appears in the above-identified patent and that said Letters Patent is hereby corrected as shown below:

In the Claims

COLUMN 8, LINE 19 Claim 1
Delete “selling/detaching part” and insert --setting/detaching part--.

Signed and Sealed this
Twenty-fifth Day of August, 2015

Michelle K. Lee

Michelle K. Lee
*Director of the United States Patent and Trademark Office*